US007749982B2

(12) United States Patent
Freiss et al.

(10) Patent No.: US 7,749,982 B2
(45) Date of Patent: Jul. 6, 2010

(54) COMPLEX CONTAINING MEQUITAZINE, A CYCLODEXTRIN AND AN INTERACTION AGENT

(75) Inventors: Bernard Freiss, Castres (FR); Hubert Lochard, Albi (FR)

(73) Assignee: Pierre Fabre Medicament, Boulogne-Billancourt (FR)

( * ) Notice: Subject to any disclaimer, the term of this patent is extended or adjusted under 35 U.S.C. 154(b) by 436 days.

(21) Appl. No.: 11/665,839

(22) PCT Filed: Oct. 19, 2005

(86) PCT No.: PCT/EP2005/055388

§ 371 (c)(1),
(2), (4) Date: Apr. 19, 2007

(87) PCT Pub. No.: WO2006/042857

PCT Pub. Date: Apr. 27, 2006

(65) Prior Publication Data

US 2007/0293454 A1    Dec. 20, 2007

(30) Foreign Application Priority Data

Oct. 21, 2004    (FR)  .................................. 04 11202

(51) Int. Cl.
*A61K 31/724*   (2006.01)
*A61K 31/5415*  (2006.01)
(52) U.S. Cl. ...................... 514/58; 514/225.2
(58) Field of Classification Search ................ None
See application file for complete search history.

(56) References Cited

U.S. PATENT DOCUMENTS

| 4,975,426 | A | * | 12/1990 | Sunshine et al. ............. 514/159 |
| 5,570,596 | A | | 11/1996 | Masahiro et al. |
| 5,770,596 | A | | 6/1998 | Coquelet et al. |
| 6,255,502 | B1 | | 7/2001 | Penkler et al. |
| 6,414,050 | B1 | | 7/2002 | Howdle et al. |
| 7,390,411 | B2 | | 6/2008 | Fages et al. |
| 2004/0119179 | A1 | | 6/2004 | Perrut et al. |
| 2005/0274671 | A1 | | 12/2005 | Fages et al. |
| 2006/0246140 | A1 | | 11/2006 | Lochard et al. |
| 2007/0270379 | A1 | | 11/2007 | Friess |

FOREIGN PATENT DOCUMENTS

| EP | 0089860 | * | 2/1983 |
| EP | 0153998 | A2 | 9/1985 |
| EP | 1018340 | * | 7/2000 |
| EP | 0991407 | B9 | 11/2001 |
| EP | 1018340 | B1 | 9/2003 |
| FR | 2 034 605 | | 12/1970 |
| FR | 2 742 053 | A1 | 6/1997 |
| FR | 2 788 436 | A1 | 7/2000 |
| FR | 2 815 540 | A1 | 4/2002 |
| FR | 2 830 760 | A1 | 4/2003 |
| GB | 1250534 | | 10/1971 |
| WO | WO-02/089851 | A1 | 11/2002 |
| WO | WO-03/030867 | A2 | 4/2003 |
| WO | WO03/043604 | * | 5/2003 |
| WO | WO-2004/096284 | A1 | 11/2004 |
| WO | WO-2005/097201 | A2 | 10/2005 |

OTHER PUBLICATIONS

Yang et al., Chromatographia, vol. 62, No. 7, Oct. 2005, pp. 441-445.
Veiga et al., Drug Development and Industrial Pharmacy, vol. 23, No. 7, 1997, pp. 721-725.
Ylitalo et al., International Journal of Clinical Pharmacology Research, vol. 9, No. 5, 1989, pp. 305-308 (Abstract Only).
Rajewski et al., Journal of Pharmaceutical Sciences, vol. 85, No. 11, Nov. 1996, pp. 1142-1169.
Sweetman (Ed.), "Martindale: The Complete Drug reference",Pharmaceutical Press, 2002, pp. 421: "Miquitazine".
Database WPI, Section Ch, Week 199007, Derwent PUblications Ltd., London, GB; Class B02, AN 1990-049219, XP002380356 & JP 02 003610 A (TOYO JOZO KK) Jan. 9, 1990.
Veiga et al., "Dissolution studies of mequitazine in several dissolution media with sodium lauryl sulfate, Tween 20 and β—cyclodextrin", World Meeting on Pharmaceutics, Biopharaceutics and Pharmaceutical Technology, 1st, Budapest, May 9-11, 1995, 725-6 Publisher: APGI, Chatenay Malabry, FR. Coden: 62JJAQ, pp. 625-626.
Mura et al., International Journal of Pharmaceutics, vol. 260, 2003, pp. 293-302.
Database WPI, Section Ch, Week 199312, Derwent Publications Ltd., London, GB; Class A96, AN 1993-098122, XP002375837 & KR 9 206 911 B (Shin Poong Pharm Co), Aug. 22, 1992.
Van Hees et al., Journal of Inclusion Phenomena and Macrocyclic Chemistry, vol. 44, 2002, pp. 271-274.
Van Hees et al., Pharmaceutical Research, vol. 16, No. 12, 1999, pp. 1864-1870.
Redenti et al., "Drug/Cyclodextrin/Hydroxy Acid Multicomponent Systems. Properties and Pharmaceutical Applications", Journal of Pharmaceutical Sciences, Jan. 2000, vol. 89, No. 1, pp. 1-8, Wiley-Liss, Inc. and the American Pharmaceutical Association.
Buvari-Barcza et al., "Ternary β-Cyclodextrin Complexes as Models of Allosteric Effects", Journal of Inclusion Phenomena and Macrocyclic Chemistry, 2002, vol. 42, pp. 209-212, Kluwer Academic Publishers.
Mura et al., "Multicomponent Systems of Econazole with Hydroxyacids and Cyclodextrins", Journal of Inclusion Phenomena and Macrocyclic Chemistry, 2001, vol. 39, pp. 131-138, Kluwer Academic Publishers.

(Continued)

*Primary Examiner*—Leigh C Maier
(74) *Attorney, Agent, or Firm*—Birch, Stewart, Kolasch & Birch, LLP.

(57) ABSTRACT

The present invention relates to a complex that includes mequitazine, a cyclodextrin, and an interaction agent wherein the rate of solubilization in water of complexed mequitazine, measured for a 2 g/l mixture of mequitazine in water at 35° C. after 15 minutes of stirring, is greater than 50% at pH 9. The present invention also relates to a method of preparing the aforementioned complex and a pharmaceutical composition of which the complex is a part.

15 Claims, 1 Drawing Sheet

OTHER PUBLICATIONS

Piel et al., "Study of the Influence of Both Cyclodextrins and L-Lysine on the Aqueous Solubility of Nimesulide; Isolation and Characterization of Nimesulide-L-Lysine-Cyclodextrin Complexes", Journal of Pharmaceutical Sciences, Apr. 1997, vol. 86, No. 4, American chemical Society and American Pharmaceutical Association.

Barillaro et al., "Inclusion of Miconazole into Cyclodextrins by Means of Supercritical Carbon Dioxide: Influence of the Addition of an Acidic Ternary Compound", Proceedings of the 6th International Symposium on Supercritical Fluids, Versallies, 2003, pp. 1897-1902.

Jung et al., "Particle design using supercritical fluids: Literature and patent survey", Journal of Supercritical Fluids, 2001, vol. 20, pp. 179-219, Elsevier Science B.V.

Kamihara et al., "Formation of Inclusion Complexes between Cyclodextrins and Aromatic Compounds under Pressurized Carbon Dioxide", Journal of Fermentation and Bioengineering, 1990, vol. 69, No. 6, pp. 350-353.

Subramaniam et al., "Pharmaceutical Processing with Supercritical Carbon Dioxide", Journal of Pharmaceutical Sciences, Aug. 1997, vol. 86, No. 8, American Chemical Society and American Pharmaceutical Association.

Van Hees et al., "Inclusion of Piroxicam into $\beta$-Cyclodextrin by Means of Supercritical Carbon Dioxide: Thermal, Spectroscopic and Physicochemical Studies", J. Pharm. Beig., 2000, vol. 55, No. 1, pp. 30-31.

* cited by examiner

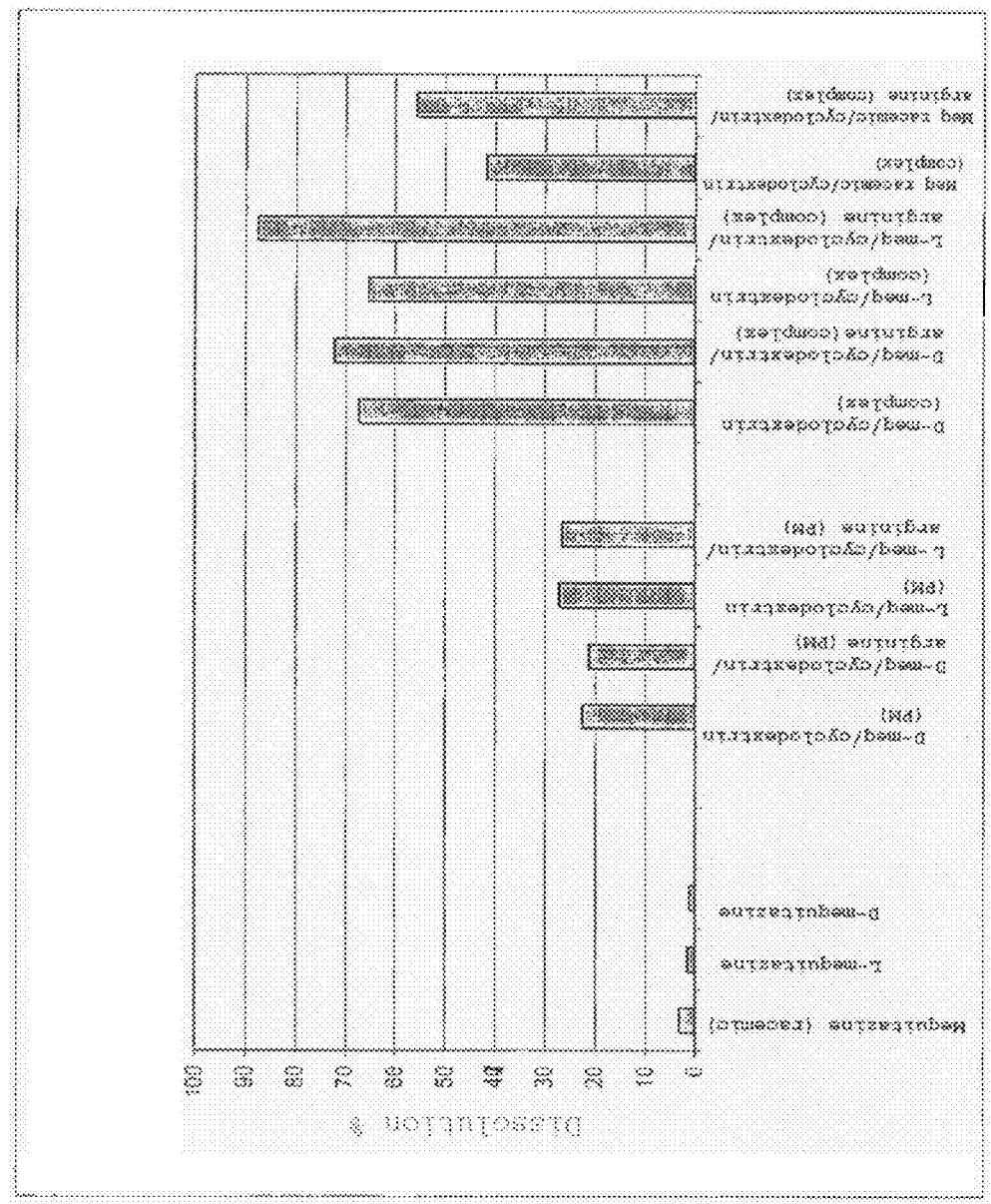

COMPLEX CONTAINING MEQUITAZINE, A CYCLODEXTRIN AND AN INTERACTION AGENT

The present invention relates to complexes of mequitazine, cyclodextrins, and an interaction agent, as such complexes have much higher solubility compared to mequitazine considered alone.

Numerous pharmaceutically active substances present low solubility in aqueous media and consequently in biological media. Such solubility leads to low bioavailability and as a result doses administered must be increased. Such an increase is not always without consequences both with respect to side effects as well as from an economic point of view when considering the high cost of the pharmaceutically active ingredients.

Mequitazine is an antihistamine used for the treatment of allergies. The mequitazine molecule was specifically described in patent FR 2 034 605.

Mequitazine is generally administered by oral route in a variety of forms such as syrup, tablets, or gel caps, for example.

As for many pharmaceutically active ingredients, the absorption of mequitazine administered by oral route takes place in the intestine. However, it has been observed by the applicant that the bioavailability of this active ingredient is very low, on the order of 0.3%, which could be explained by its low solubility. A very small portion of the mequitazine ingested is in solubilized form, and thus it is absorbed with difficulty through the intestinal barrier.

There are various pharmaceutical publications and patents relating to the production of interaction complexes of active ingredients with cyclodextrins, and this with the aim of improving their solubility. However, none specifically relates to mequitazine in the form of a racemic mixture or of one of its enantiomers.

Patent FR 2 742 053 describes an aqueous formulation intended for the local treatment of ocular allergies. The patent also describes a collyrium that includes mequitazine and cyclodextrins in an aqueous solution. As indicated in an example in the patent, the pH of the ready-to-use collyrium described therein is adjusted to 6, a value that enables it alone to ensure complete dissolution of mequitazine. Moreover, mequitazine and cyclodextrin are simply mixed in the aqueous medium and by no means is a complex created. Moreover, no interaction agent is used. The collyrium described in the patent is neither intended for oral administration nor to be subjected to a change in pH. Lastly, no allusion is made as to the bioavailability of mequitazine. Indeed, in the aforementioned document this problem does not arise because it involves local application to the eye and not administration orally.

Thus it should be noted that there is a need with regard to a pharmaceutical formulation containing mequitazine as an active ingredient which overcomes the low bioavailability of the current formulations which result from the low solubility of mequitazine when administered orally.

With regard to the simple manufacture of a medicine such as a syrup, solubility is not an obstacle to the formulation of mequitazine because mequitazine presents high solubility in an acid pH range from 2 to 6. Thus, for a liquid formulation such as described in FR 2 742 053, it is sufficient to be placed in an acid pH range to ensure complete mequitazine solubility. On the other hand, as neutrality is approached then surpassed, solubility breaks down, and it is in this case that the difficulties related to solubility and bioavailability arise since, as stated above, the pH of the intestinal juice is in an approximate range of 7 to 9.

The aim of the present invention thus consists of providing a solid form of mequitazine that presents a satisfactory solubility in an extended pH range, in particular at basic pH. Thus, in the cases measured here, solubility is most often measured at a pH of approximately 9.

The present invention thus has as an aim a complex that includes mequitazine, a cyclodextrin, and an interaction agent wherein the rate of solubilization in water of complexed mequitazine measured for a 2 g/l mixture of mequitazine in water at 35° C. after 15 minutes of stirring, is greater than 50% at pH 9.

The mequitazine/cyclodextrin/interaction agent complex according to the present invention is in solid form.

BRIEF DESCRIPTION OF THE DRAWINGS

FIG. 1 represents the rates of solubilization of mequitazine for the various samples tested.

The mequitazine contained in the complexes according to the present invention can be presented in racemic form or enantiomer form, namely L-mequitazine or D-mequitazine. The present invention thus relates to complexes of a cyclodextrin and racemic mequitazine, complexes of a cyclodextrin and D-mequitazine, and/or complexes of a cyclodextrin and L-mequitazine, all of these complexes including moreover an interaction agent.

Additionally, it has been noted that when the complexes involve one mequitazine enantiomer only, either D- or L-, the rate of solubilization in water of complexed mequitazine according to the present invention is advantageously greater than 60% at pH 9, more advantageously greater than 70% at pH 9.

Moreover, it has been noted that when the complexes involve the L-enantiomer only, the rate of solubilization in water of the complexed mequitazine according to the present invention is advantageously greater than 80% at pH 9.

Such complexes make it possible to propose and formulate mequitazine in soluble form, therefore easily assimilable, across the physiological pH range and in particular at a pH of approximately 7 to 10 and more advantageously of approximately 8 to 9. Indeed, as previously indicated, the pH of the intestinal milieu ranges between approximately 7 and approximately 9, and it is precisely there that mequitazine is absorbed. The fact of ensuring a particularly increased solubility at these pH is an undeniable advantage of the present invention. As an indication, measured under the same conditions, the rate of solubilization of mequitazine alone, which is to say not complexed, is about 1%. Thus, the present invention makes it possible to increase the solubility of this molecule by a factor of at least 30, even 60, and even 80.

Thus, the addition of an interaction agent to the mequitazine/cyclodextrin complex according to the present invention makes it possible to increase the solubilization of mequitazine.

In the sense of the present invention, "interaction agent" means any organic or mineral agent that improves the physicochemical properties, in particular the properties of solubilization in aqueous media, of the mequitazine/cyclodextrin complex by noncovalent interactions with the mequitazine included in the cyclodextrin or directly with the mequitazine/cyclodextrin complex. Advantageously, the interaction agent is either a surfactant, for example sodium laurel sulfate or Tween, an acid, or a base. Advantageously, it is an acid or a base.

In an advantageous way, the interaction agent is selected from among an amino acid, a carboxylic acid, an acetate, a carboxylate, an amine, or ammonia. In an even more advantageous way, is selected from among acetic acid, tartaric acid, citric acid, gluconic acid, malic acid, lactic acid, maleic acid, fumaric acid, L-lysine, L-valine, L-isoleucine, L-arginine, and ammonia. Advantageously, it is an amino acid, in an advantageous way a basic amino acid. Arginine is particularly preferred, advantageously in its L-form.

The present invention also relates to the use of the complex according to the present invention to increase the solubility and the bioavailability of mequitazine at basic pH, advantageously in the range between 7 and 10, and in an advantageous way still between 8 and 9. The preferred interaction agent is arginine, and the invention thus relates to mequitazine/cyclodextrin/arginine complexes and their use to increase mequitazine solubility and bioavailability at basic pH, advantageously in the range between 7 and 10, and in an advantageous way still between 8 and 9.

Advantageously the cyclodextrin is selected from among the group consisting of the cyclodextrins, modified cyclodextrins, and their mixture. In an advantageous way, it is β-cyclodextrin, methyl-β-cyclodextrin, γ-cyclodextrin, or hydroxypropyl-β-cyclodextrin. Advantageously, it is β-cyclodextrin.

In the sense of the present invention, "rate of solubilization" means the percentage of solubilized mequitazine after stirring a mixture of water and mequitazine for 15 minutes at 37° C. A mixture of 2 g/l of mequitazine in water is usually used to measure this rate. This solubilization can be measured by a solubilization test as indicated below.

MEQUITAZINE SOLUBILIZATION TEST

Experimental Protocol:
The mequitazine content in the dissolution solutions is measured by HPLC:

Equipment Used:
Waters HPLC System:
Separation module 2695,
UV detector 2487.

Chromatographic Conditions:
Column: μBondapak 125A, 10 μm, 150×4.6 mm
Mobile phase:
90%: 500 ml water/500 ml acetonitrile/1 ml phosphoric acid,
10%: 500 ml water/0.5 ml phosphoric acid.
Flow rate: 1 ml/min
Wavelength detector: 256 nm
Detector sensitivity: 2 AUFS
Volume injected: 20 μl
Oven temperature: 25° C.
Analysis period: 12 minutes Preparation of the Control Solutions:
Control solution: SM: Place 50 mg of control mequitazine in a 100 ml flask. Dissolve with 20 ml of dimethylformamide and bring up to volume with methanol.
Range:
T1: 1:20 dilution of T3 in water/acetonitrile (50/50),
T2: 1:10 dilution of T3 in water/acetonitrile (50/50),
T3: 1:100 dilution of SM in water/acetonitrile (50/50),
T4: 1:50 dilution of SM in water/acetonitrile (50/50),
T5: 1:20 dilution of SM in 50% water/50% acetonitrile.

Procedure for Solubility Tests at 2 g/l:

Test Procedure:
In a 100 ml Erlenmeyer flask, place a test sample equivalent to 100 mg of mequitazine. Add 50 ml of ultrapure water. The pH obtained is approximately 9.5. Place under magnetic stirring at 400 rpm in a water bath at 37° C.±2° C. Remove a 2 ml sample under magnetic stirring at 15 minutes. Filter the sample on a 0.45 μm Gelman GHP Acrodisc polypropylene filter. The solution must be limpid. Dilute the sample to 1/200 in a phase: water/acetonitrile (50/50).

Methodology, Presentation of Results:
Inject 20 μl of each control solution.
Perform a linear regression of the mequitazine peak surfaces with respect to the concentrations. The correlation coefficient must be greater than 0.995.
Inject 20 μl of the solutions to be examined.
Measure the area of the peak of mequitazine in each solution to be examined.
Deduce concentration X in μg/ml by following the regression line of the controls.
Calculate the concentration in μg/ml of solubilized mequitazine by multiplying by the inverse of the dilution made (i.e., 200).

The rate of solubility of mequitazine is calculated by dividing the concentration of solubilized mequitazine by the total concentration of mequitazine in the starting solution. The mequitazine/cyclodextrin/interaction agent complexes are likely to be obtained by a process such as described hereafter.

A method of preparing a complex according to the present invention includes the following successive steps:
a) placing mequitazine in contact with a cyclodextrin and an interaction agent;
b) implementing a molecular diffusion step by placing in contact in static mode a dense fluid under pressure with the mixture obtained in step (a) in the presence of one or more diffusion agents;
c) recovering the mequitazine/cyclodextrin/interaction agent complex thus formed.

The complex thus recovered in step (c) is in solid form. However, it may still contain some water molecules or be moist. In order to eliminate any trace of water, in another advantageous embodiment, step (c) is followed by a step (d) of drying the complex, advantageously between 60° C. and 80° C., advantageously at 60° C. and in an advantageous way overnight. This drying, which is optional, thus makes it possible to remove any trace of residual water present in the complex following step (c).

The step of molecular diffusion in static mode, step (b), termed the maturation step, essentially consists of a molecular diffusion phase in a dense milieu under pressure, and in particular supercritical, that enables mequitazine to be included in cyclodextrins. The objective sought during this phase of diffusion is to form inclusion complexes between mequitazine, the cyclodextrin, and the interaction agent. The complex thus formed associates mequitazine, the cyclodextrin, and the interaction agent noncovalently. The interaction agent interacts according to two plausible hypotheses: strong interactions with the mequitazine included in the cyclodextrin and/or strong interactions with the complex formed.

The presence of this interaction agent primarily makes it possible to improve the dissolution properties of the complex in biological liquids, in particular water, and to possibly increase the rate of inclusion of mequitazine in the cyclodextrin.

The improvement of the physicochemical properties, in particular in terms of dissolution of the system formed may originate in:
- noncovalent interaction of the interaction agent with mequitazine, the cyclodextrin, or both (complexation, salification, etc.),
- local pH variation in the dissolution medium,
- presence of an eutectic system,
- modification of the interface between the system and its dissolution medium (surfactant effect, granulometric change).

In the sense of the present invention, "dense fluid under pressure" means any fluid used at a temperature or a pressure greater than its critical value. Advantageously $CO_2$ may be used pure or as mixture with an organic solvent classically used by those skilled in the art.

In the sense of the present invention, "diffusion agent" means any solvent that favors an interaction of mequitazine with a cyclodextrin.

Advantageously, this diffusion agent is selected from among the group consisting of the alcohols, ketones, ethers, esters, and water, with or without a surfactant, and their mixtures. In an even more advantageous way, water is selected.

In the sense of the present invention, "static mode" means a reaction or a process in which all of the reagents are simultaneously placed together and where the reaction is allowed to progress. For example, in step (b) of the present invention, into an autoclave are placed the substances of the complex, water, and supercritical $CO_2$, and the reaction is allowed to progress for several hours. The mass of the product does not change during the reaction. On the contrary, in dynamic mode, the reagents are supplied as the reaction or production progresses. Often within the framework of dynamic mode, there is circulation of a fluid. The mass of the product changes during production.

In an advantageous way, molecular diffusion step (b) of the method according to the present invention is carried out under stirring.

In a particular embodiment of the invention, during step (a) mequitazine, the interaction agent, and the cyclodextrin are introduced in solid or liquid form into a receptacle into which during step (b) is injected the dense fluid under pressure and the diffusion agent in judiciously selected proportions. Pressure and temperature conditions, as well as the duration of treatment, are defined by any suitable method.

The diffusion agent can be added continuously or discontinuously in a quantity ranging between 1 and 50% in mass compared to the total mass of the mixture, preferably between 10 and 25% in mass compared to total mass of the mixture.

The time necessary for the molecular diffusion in step (b) is determined by any suitable method. Step (b) may be repeated as many times as desired to obtain a satisfactory rate of dissolution. Advantageously, step (b) lasts between approximately 1 and 16 hours, advantageously 2 hours.

The pressure and temperature conditions in step (b) are chosen in a way to favor molecular diffusion. Advantageously the pressure of the supercritical fluid lies between 0.5 MPa and 50 MPa, advantageously 15 MPa, and the temperature between 0 and 200° C., advantageously 75° C.

Advantageously step (b) of the process is implemented in a closed reactor, in particular an autoclave.

The process can be implemented in batches or continuously. In an advantageous way the process according to the present invention is carried out in batches.

The mequitazine/cyclodextrin/interaction agent molar ratio can be chosen in a way to ensure optimal inclusion of mequitazine within the cyclodextrins. Thus, advantageously the mequitazine/cyclodextrin molar ratio lies between 1/1 and 1/10, advantageously between 1/1 and 1/5, and in an advantageous way between 1/2 and 1/3. In the same advantageous way the mequitazine/interaction agent molar ratio lies between 1/1 and 1/10, advantageously between 1/1 and 1/5, and in an advantageous way between 1/1 and 1/3.

Advantageously, step (b) of the process is implemented in a closed reactor, possibly under stirring, supplied with the dense fluid and the mequitazine solution, continuously if need be.

The present invention relates moreover to a pharmaceutical composition, intended to be administered by oral route, that includes a complex according to the present invention, and possibly a pharmaceutically acceptable excipient.

It concerns moreover a complex according to the present invention or a pharmaceutical composition according to the present invention for its use as a drug, advantageously intended to treat allergies.

The following examples, given as indications, were carried out with mequitazine in racemic form and/or D- or L-enantiomer form, with the additional use of β-cyclodextrin, water as a diffusion agent, and arginine as an interaction agent.

COMPARATIVE EXAMPLE 1

Creation of Mequitazine/β-cyclodextrin Complexes 2.5 grams of mequitazine in racemic or L- or D-form, 20.11 grams of β-cyclodextrin, and 5.11 grams of water are mixed and introduced into a 500 ml reactor. Carbon dioxide is then introduced into the reactor under a pressure of 15 MPa and at a temperature of 75° C. The unit is maintained under these operating conditions for 2 hours. The powder thus collected after releasing the medium is placed in a drying oven at 60° C. overnight.

The solubility and the rates of solubilization of complexed mequitazine (D, L, or racemic) are measured as indicated above in the "mequitazine solubilization test". The results are collected in Table 1 and represented in FIG. 1 below.

EXAMPLE 2

Creation of Mequitazine/β-cyclodextrin/arginine Complexes

The procedure is identical to that of Example 1, only the quantities of the reagents change. 2.5 grams of mequitazine in racemic or L- or D-form, 20.11 grams of β-cyclodextrin, 1.35 grams of arginine, and 5.63 grams of water are used.

The solubility and the rates of solubilization of complexed mequitazine (D, L, or racemic) are measured as indicated above in the "mequitazine solubilization test". The results are collected in Table 1 and represented in FIG. 1 below.

COMPARATIVE EXAMPLE

Solubility of racemic, L-, and D-mequitazine taken separately and physical mixtures of mequitazine/β-cyclodextrin and mequitazine/β-cyclodextrin/arginine Moreover, the rates of solubilization of the mequitazine obtained thanks to the use of the complexes according to the present invention are compared with the rates of solubilization obtained with the simple cyclodextrin/mequitazine mixture and optionally an interaction agent, such a mixture is called a "physical mixture" and has nothing in common with complexes.

Creation of a "Physical Mixture":

A "physical mixture" corresponds to the simple mixture of the components but in a non-complexed form. It is thus a question of using the molar ratios of mequitazine/cyclodextrin and possibly arginine as interaction agent used to create the complexes, and to carry out solubility tests on these "physical mixtures".

Thus the superiority of the complexes according to the present invention can be demonstrated, in particular compared to simple physical mixtures which correspond, for example, to the product described in patent application FR 2 742 053.

The solubility and the rates of solubilization of mequitazine only or mequitazine in physical mixtures are measured as indicated above in the "mequitazine solubilization test".

The solubilization results are collected in Table 1 and represented in FIG. 1 below.

TABLE 1

Rate of solubilization of mequitazine in the various samples: mequitazine alone, in a simple physical mixture, or in complex with cyclodextrin or cyclodextrin and arginine.

| Active ingredient alone | | pH | Quantity of mequitazine dissolved in µg/ml | Rate of solubilization (%) |
|---|---|---|---|---|
| Ex 3 | racemic | 9 | 60 | 3 |
| Ex 3 | L-mequitazine | 9 | 32 | 1.6 |
| Ex 3 | D-mequitazine | 9 | 26 | 1.3 |
| Physical mixtures | | | | |
| Ex 3 | D-meq/cyclodextrin | 9.7 | 449 | 22.45 |
| Ex 3 | D-meq/cyclodextrin/ arginine | 9.9 | 423 | 21.15 |
| Ex 3 | L-meq/cyclodextrin | 9.8 | 540 | 27 |
| Ex 3 | L-meq/cyclodextrin/ arginine | 9.8 | 529 | 26.45 |
| Complexes | | | | |
| Ex 1 | D-meq/cyclodextrin | 9.3 | 1345 | 67.25 |
| Ex 2 | D-meq/cyclodextrin/ arginine | 9.1 | 1443 | 72.15 |
| Ex 1 | L-meq/cyclodextrin | 9.4 | 1308 | 65.4 |
| Ex 2 | L-meq/cyclodextrin/ arginine | 9.2 | 1750 | 87.5 |
| Ex 1 | racemic meq/ cyclodextrin | 9.7 | 832 | 41.6 |
| Ex 2 | racemic meq/ cyclodextrin/arginine | 9.2 | 1115 | 55.75 |

FIG. 1 represents the rates of solubilization of mequitazine for the various samples tested at 37° C. after 15 minutes of stirring for a 2 g/l solution of mequitazine.

Thus it can be noted that the complexes according to the present invention allow a particularly increased mequitazine solubility, to be specific at pH 9. Such a pH is particularly interesting because it corresponds to intestinal pH. It can also be noted that mequitazine alone has a very low solubility at this pH.

A difference in solubility between racemic mequitazine and when complexed with either enantiomer can also be noted. It appears that in the complexed form the enantiomer complexes have the best solubility.

It is also observed that the simple physical component mixtures, even if they make it possible to increase the rate of dissolution of mequitazine, do not make it possible to obtain results as satisfactory as those obtained with the complexes. Thus, with the complexes, the rate of dissolution is increased by a factor of approximately 3. In the same way, simple complexation without an interaction agent does not make it possible to obtain results as satisfactory as those obtained with the complexes according to the present invention.

The invention claimed is:

1. A complex that includes mequitazine, a cyclodextrin, and L-arginine, wherein the complex is in a solid form, the mequitazine is in the form of its enantiomer D- and wherein the rate of solubilization in water of complexed mequitazine measured for a 2 g/l mixture of mequitazine in water at 35° C. after 15 minutes of stirring at 400 rpm, is greater than 60% at pH 9.

2. A method of preparing a complex of claim 1 comprising the following successive steps:
    a) placing mequitazine in contact with a cyclodextrin and L-arginine and adding water;
    b) implementing a molecular diffusion step by placing in contact in static mode a dense fluid under pressure with the mixture obtained in step (a);
    c) recovering the mequitazine/cyclodextrin/L-arginine complex thus formed.

3. The process of claim 2 wherein it includes an additional step (d) of drying the complex.

4. The process of claim 2 wherein the dense fluid under pressure is carbon dioxide.

5. The process of claim 2 wherein molecular diffusion step (b) is carried out under stirring.

6. The process of claim 2 wherein water is added continuously or discontinuously in a quantity ranging between 1 and 25% in mass.

7. The process of claim 2 wherein the mequitazine/cyclodextrin molar ratio lies between 1/1 and 1/10.

8. The process of claim 2 wherein the mequitazine/L-arginine molar ratio lies between 1/1 and 1/10.

9. A pharmaceutical composition, intended to be administered by oral route, that includes a complex of claim 1.

10. A method for treating allergies comprising the administration of an effective amount of a complex of claim 1 or a pharmaceutical composition of claim 13 to a patient in need thereof.

11. The complex of claim 1 wherein the rate of solubilization in water of complexed mequitazine measured for a 2 g/l mixture of mequitazine in water at 35° C. after 15 minutes of stirring at 400 rpm is greater than 70% at pH 9.

12. The method of claim 3 wherein step (d) is carried out at a temperature ranging between 60 and 80° C.

13. The method of claim 6 wherein water is added continuously or discontinuously in a quantity ranging between 10 and 25% in mass.

14. The method of claim 7 wherein the mequitazine/cyclodextrin molar ratio lies between 1/2 and 1/3.

15. The method of claim 8 wherein the mequitazine/L-arginine molar ratio lies between 1/1 and 1/3.

* * * * *

UNITED STATES PATENT AND TRADEMARK OFFICE
CERTIFICATE OF CORRECTION

PATENT NO. : 7,749,982 B2  
APPLICATION NO. : 11/665839  
DATED : July 6, 2010  
INVENTOR(S) : Freiss et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 438 days.

Signed and Sealed this

Eighteenth Day of January, 2011

David J. Kappos  
*Director of the United States Patent and Trademark Office*